(12) United States Patent
Majano

(10) Patent No.: US 10,278,850 B2
(45) Date of Patent: May 7, 2019

(54) STENT DEPLOYMENT AND POSTDILATATION NON-COMPLIANT BALLOON CATHETER AND METHODS OF USE

(71) Applicant: Romeo Majano, Coral Gables, FL (US)

(72) Inventor: Romeo Majano, Coral Gables, FL (US)

(73) Assignee: Clever Cath Technologies, LLC, Coral Gables, FL (US)

(*) Notice: Subject to any disclaimer, the term of this patent is extended or adjusted under 35 U.S.C. 154(b) by 29 days.

(21) Appl. No.: 15/613,937

(22) Filed: Jun. 5, 2017

(65) Prior Publication Data

US 2017/0281380 A1 Oct. 5, 2017

Related U.S. Application Data

(63) Continuation-in-part of application No. 15/176,227, filed on Jun. 8, 2016, now Pat. No. 9,668,899, which
(Continued)

(51) Int. Cl.
*A61F 2/958* (2013.01)
*A61M 25/10* (2013.01)
(Continued)

(52) U.S. Cl.
CPC ............ *A61F 2/958* (2013.01); *A61F 2/2427* (2013.01); *A61M 25/0032* (2013.01); *A61M 25/10* (2013.01); *A61M 25/104* (2013.01); *A61M 25/1011* (2013.01); *A61F 2/2418* (2013.01); *A61F 2/2433* (2013.01); *A61F 2/2436* (2013.01); *A61F 2002/484* (2013.01); *A61F 2002/9583* (2013.01); *A61F 2210/0004* (2013.01); *A61F 2230/001* (2013.01); *A61F 2250/0003* (2013.01);
(Continued)

(58) Field of Classification Search
CPC ................ A61M 25/1011; A61F 2/958; A61F 2250/0098
See application file for complete search history.

(56) References Cited

U.S. PATENT DOCUMENTS

2010/0234940 A1* 9/2010 Dolan .................. A61F 2/2433
623/2.11
2010/0262227 A1* 10/2010 Rangwala ................ A61F 2/91
623/1.16
(Continued)

*Primary Examiner* — Anh T Dang
(74) *Attorney, Agent, or Firm* — Joseph E. Maenner; Maenner & Associates, LLC

(57) ABSTRACT

A method of inserting a stent includes inserting a unitary, monolithic catheter assembly into a cardiac artery. The catheter assembly includes a body having a proximal end and a distal end, a distal balloon mounted on the distal end, and a proximal balloon mounted on the body, proximally of the distal balloon. A balloon expandable stent is mounted on the distal balloon. The method further includes the steps of advancing the catheter assembly to a blockage in the artery until the distal balloon and the stent both extend across the blockage; inflating the distal balloon and expanding the stent; deflating the distal balloon; advancing the catheter body distally until the proximal balloon extends within the stent; expanding the proximal balloon to post-dilate the stent; deflating the proximal balloon; and withdrawing the catheter body from the artery.

7 Claims, 17 Drawing Sheets

Related U.S. Application Data is a continuation-in-part of application No. 15/045,833, filed on Feb. 17, 2016, now abandoned, which is a continuation-in-part of application No. 14/226,861, filed on Mar. 27, 2014, now Pat. No. 9,387,102.

(51) Int. Cl.
*A61F 2/24* (2006.01)
*A61M 25/00* (2006.01)
*A61F 2/48* (2006.01)

(52) U.S. Cl.
CPC ............... *A61F 2250/0096* (2013.01); *A61F 2250/0098* (2013.01); *A61M 2025/1084* (2013.01)

(56) References Cited

U.S. PATENT DOCUMENTS

| | | | | |
|---|---|---|---|---|
| 2010/0280451 | A1* | 11/2010 | Teeslink | A61B 17/12045 604/99.04 |
| 2014/0100647 | A1* | 4/2014 | Bourang | A61F 2/856 623/1.12 |

* cited by examiner

STENT DEPLOYMENT AND POSTDILATATION NON-COMPLIANT BALLOON CATHETER AND METHODS OF USE

CROSS-REFERENCE TO RELATED APPLICATION

The present application is a Continuation-in-Part of U.S. patent application Ser. No. 15/176,227, filed on Jun. 9, 2016 (allowed), which is a Continuation-in-Part of U.S. patent application Ser. No. 15/045,833, filed on Feb. 17, 2016, which is a Continuation-in-Part application of U.S. patent application Ser. No. 14/226,861, filed on Mar. 27, 2014 and issued on Jul. 12, 2016 as U.S. Pat. No. 9,387,102, which are all incorporated herein by reference in their entireties.

FIELD OF THE INVENTION

The present invention relates to a unitary catheter assembly that is used to deploy a bioabsorbable or other type of stent across the blockage and then post-dilate the stent after stent deployment.

BACKGROUND OF THE INVENTION

Percutaneous coronary intervention ("PCI"), or "angioplasty", is an invasive procedure that is used to open a blockage in a coronary artery, that is, an artery that provides blood to the heart. In a PCI procedure, a cardiologist inserts a catheter into an artery in the upper arm or thigh of a patient and guides the catheter through the arteries to the affected coronary artery. With the catheter in place, the doctor threads a guide wire across the blockage. After the wire is across the blockage and positioned distal to the blockage, the cardiologist then advances the catheter with a deflated balloon. The balloon is inflated to dilate the blockage to make enough room for the insertion of a second catheter with its own balloon and stent. After dilating the blockage, the balloon is deflated and the first catheter is removed proximally.

At this point in the procedure, complications can occur. For example, coronary dissections or ruptures in the wall of the artery can occur and shut down blood flow. If the guide wire, which is in position across the blockage, is lost or pulled back proximal of the blockage during the first catheter exchange, such an occurrence can result in a heart attack if rewiring the artery is not possible after breakage of the wall.

Assuming that such complications do not occur, the second catheter with another balloon and a stent or metal mesh surrounding the balloon is advanced distally along the guide wire to the area of the blockage. The second balloon is inflated, which expands the stent and completely opens the blockage. The second balloon is then deflated, leaving the stent in place, and the second catheter is then removed.

An improved device for performing the above procedure without requiring the insertion and removal of two separate catheters is required.

BRIEF SUMMARY OF THE INVENTION

Briefly, the present invention provides a method of inserting a stent by inserting a unitary, monolithic catheter into a cardiac artery. The catheter assembly includes a body having a proximal end and a distal end, a distal balloon mounted on the distal end, and a proximal balloon mounted on the body, proximally of the distal balloon. A balloon expandable stent is mounted on the distal balloon. The method further includes the steps of advancing the catheter assembly to a blockage in the artery until the distal balloon and the stent both extend across the blockage; inflating the distal balloon and expanding the stent; deflating the distal balloon; advancing the catheter body distally until the proximal balloon extends within the stent; expanding the proximal balloon to post-dilate the stent; deflating the proximal balloon; and withdrawing the catheter body from the artery.

Further, the present invention provides a catheter assembly including a body having a proximal end and a distal end, a distal balloon mounted on the distal end, and a proximal, non-compliant balloon mounted on the body, proximally of the distal balloon. A balloon expandable stent is mounted on the distal balloon.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

Figure 1:
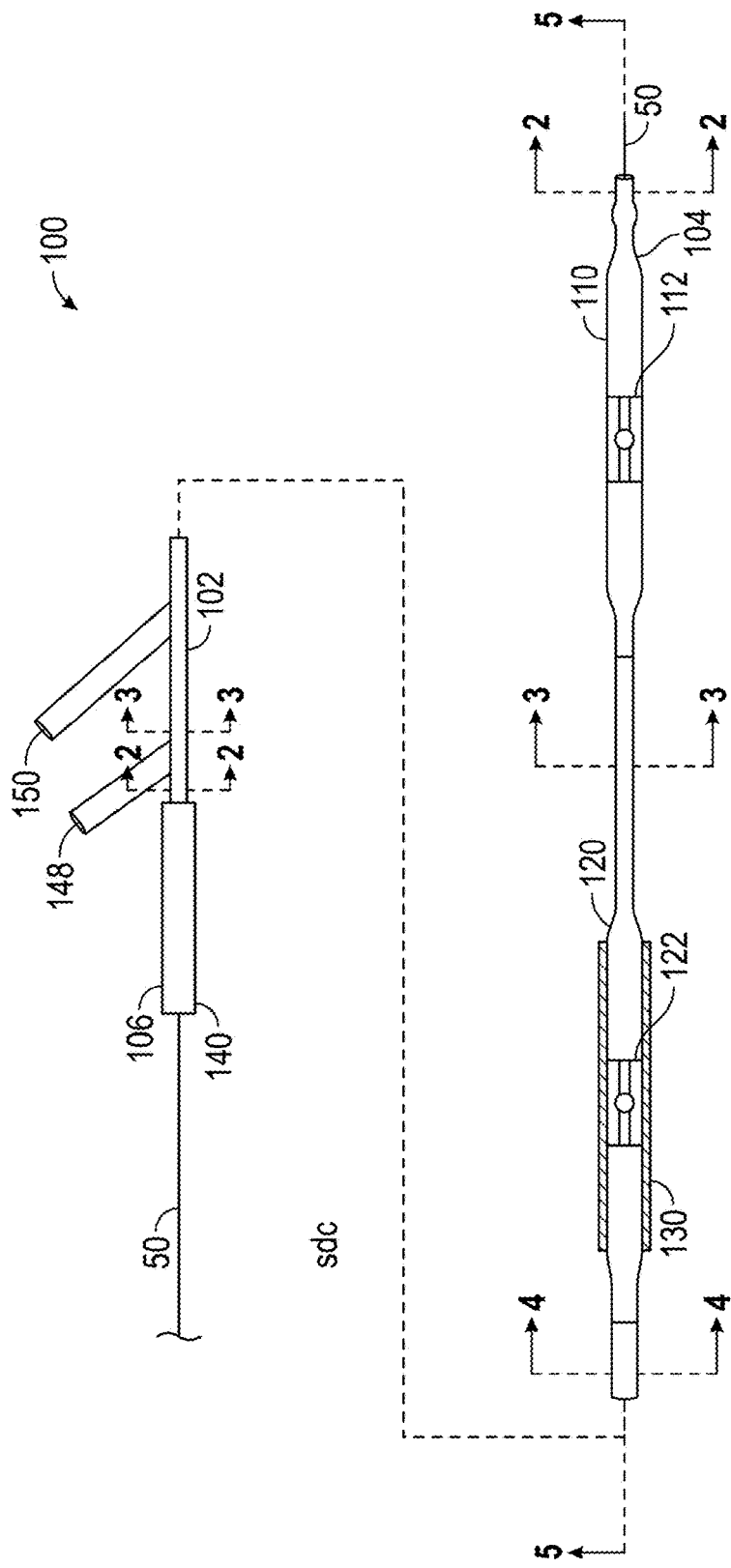
FIG. 1 is a side elevational view of a sheathless catheter assembly according to a first embodiment of the present invention.

In the drawings, like numerals indicate like elements throughout. Certain terminology is used herein for convenience only and is not to be taken as a limitation on the present invention. The terminology includes the words specifically mentioned, derivatives thereof and words of similar import. As used herein, the term "fluid" can mean and material that flows, including a liquid or a gas. The term "proximal" defines a location closer to the inserting physician and the term "distal" defines a location farther from the inserting physician. The term "about" is interpreted to mean a range of ±10% of the listed value.

The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Referring to FIGS. 1-5, a first exemplary embodiment of a catheter assembly 100 according to the present invention is shown. Catheter assembly 100 is used to open up blockages within coronary arteries.

Catheter assembly 100 is specifically designed for use within narrow coronary arteries that have an inside diameter of typically 6 French or less. The fact that catheter assembly 100 is sheathless allows catheter assembly 100 to be inserted into such narrow arteries. Sheathed catheters are too wide in diameter to fit into these arteries, given the additional width of the sheath itself.

Catheter assembly 100 has a unitary catheter body 102 that incorporates a predilatation balloon 110 at a distal end 104 of body 102 and a combination stent balloon 120 and stent 130 are located proximally of predilatation balloon 110. In an exemplary embodiment, predilatation balloon 110 has a deflated diameter of about 2.5 millimeters and a length of about 15 millimeters. Also, stent balloon 110 can include a radiopaque marker 112 disposed on an exterior thereof to allow for imaging and locating stent balloon 110 within a blood vessel 52 (shown in FIG. 8) during an angioplasty procedure.

In an exemplary embodiment, stent balloon 120 and stent 130 are located between about 10 millimeters and about 15 millimeters proximally from predilatation balloon 110. In an exemplary embodiment, catheter body 102 can be constructed from polytetrafluoroethylene, although those skilled in the art will recognize that catheter body 102 can be constructed from other material. Further, each of predilatation balloon 110 and stent balloon 120 inflate upon introduction of an inflation fluid therein, and contract toward their original size upon release or withdrawal of the inflation fluid from inside each of predilatation balloon 110 and stent balloon 120.

Figure 2:
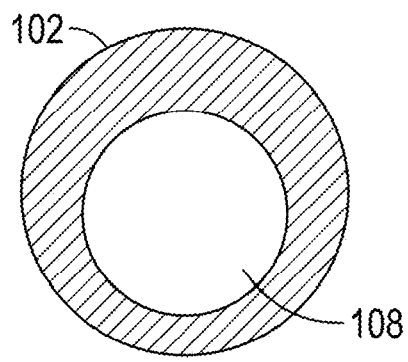
FIG. 2 is a sectional view of the sheathless catheter assembly of FIG. 1, taken along lines 2-2 of FIG. 1.

Catheter assembly 100 also includes a proximal end 106. As shown in FIG. 2, catheter assembly 100 includes a guide wire lumen 108 that extends from proximal end 106, through catheter body 102, to distal end 104. Guide wire lumen 108 is sized to allow a guide wire 50 to extend fully therethrough between proximal end 102 and distal end 104.

Figure 3:
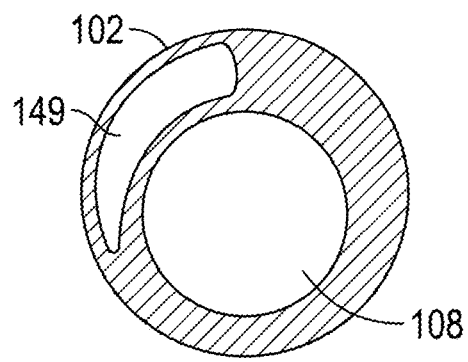
FIG. 3 is a sectional view of the sheathless catheter assembly of FIG. 1, taken along lines 3-3 of FIG. 1.
Figure 5:
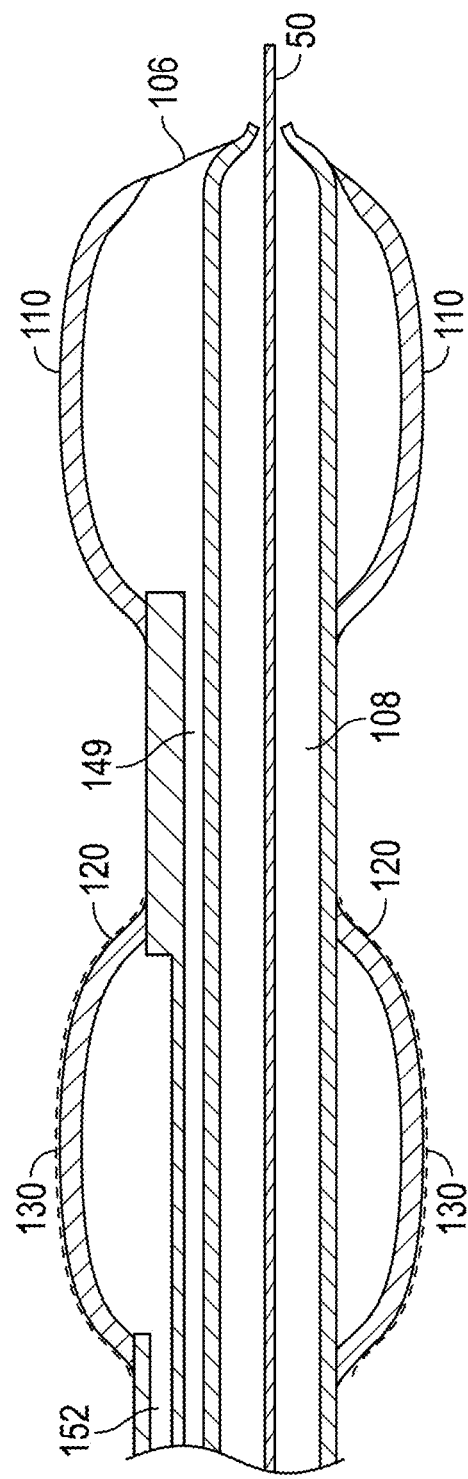
FIG. 5 is a sectional view of the sheathless catheter assembly of FIG. 1, taken along lines 5-5 of FIG. 1.

A predilatation balloon inflation connection 148 is located distally of proximal end 106. Predilatation balloon inflation connection 148 is releasably connectable to an inflation source (not shown) that provides an inflation fluid such as, for example, saline, to inflate predilatation balloon 110. As shown in FIGS. 3 and 5, a predilatation inflation lumen 149 provides fluid communication between predilatation balloon inflation connection 148 and predilatation balloon 110. Predilatation inflation lumen 149 extends through stent balloon 120.

A stent balloon inflation connection 150 is located distally of predilatation balloon inflation connection 148. While stent balloon inflation connection 150 is shown as being located distally of predilatation balloon inflation connection 148, those skilled in the art will recognize that stent balloon inflation connection 150 can be located proximally of predilatation balloon inflation connection 148 without departing from the scope of the present invention.

Figure 4:
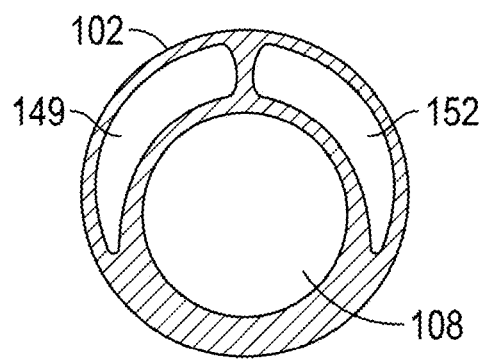
FIG. 4 is a sectional view of the sheathless catheter assembly of FIG. 1, taken along lines 4-4 of FIG. 1.

Stent balloon inflation connection 150 is releasably connectable to an inflation source (not shown) that provides an inflation fluid such as, for example, saline, to inflate stent balloon 120. The same fluid source that is used to inflate predilatation balloon 110 can be used to inflate stent balloon 120. As shown in FIGS. 4 and 5, a stent balloon inflation lumen 152 provides fluid communication between stent balloon inflation connection 150 and stent balloon 120. Referring back to FIG. 1, stent balloon 120 includes at least one radiopaque marker 122 that allows the treating physician to locate stent balloon 120 within blood vessel 52.

Stent 130 is an expandable stent as is well known in the art. Stent 130 is not self-expanding, but is expanded by the inflation of stent balloon 120. Stent 130 remains expanded after stent balloon 120 is deflated. Further, in an exemplary embodiment, stent 130 has an expanded size of customarily known, industry standard, and well-used coronary stents within typical ranges of between about 2.5 millimeters and about 4 millimeters in diameter and between about 12 millimeters and about 33 millimeters in length. Additionally, in an exemplary embodiment, stent 130 does not include a graft, although those skilled in the art will recognize that a graft may be utilized with stent 130.

Figure 6:
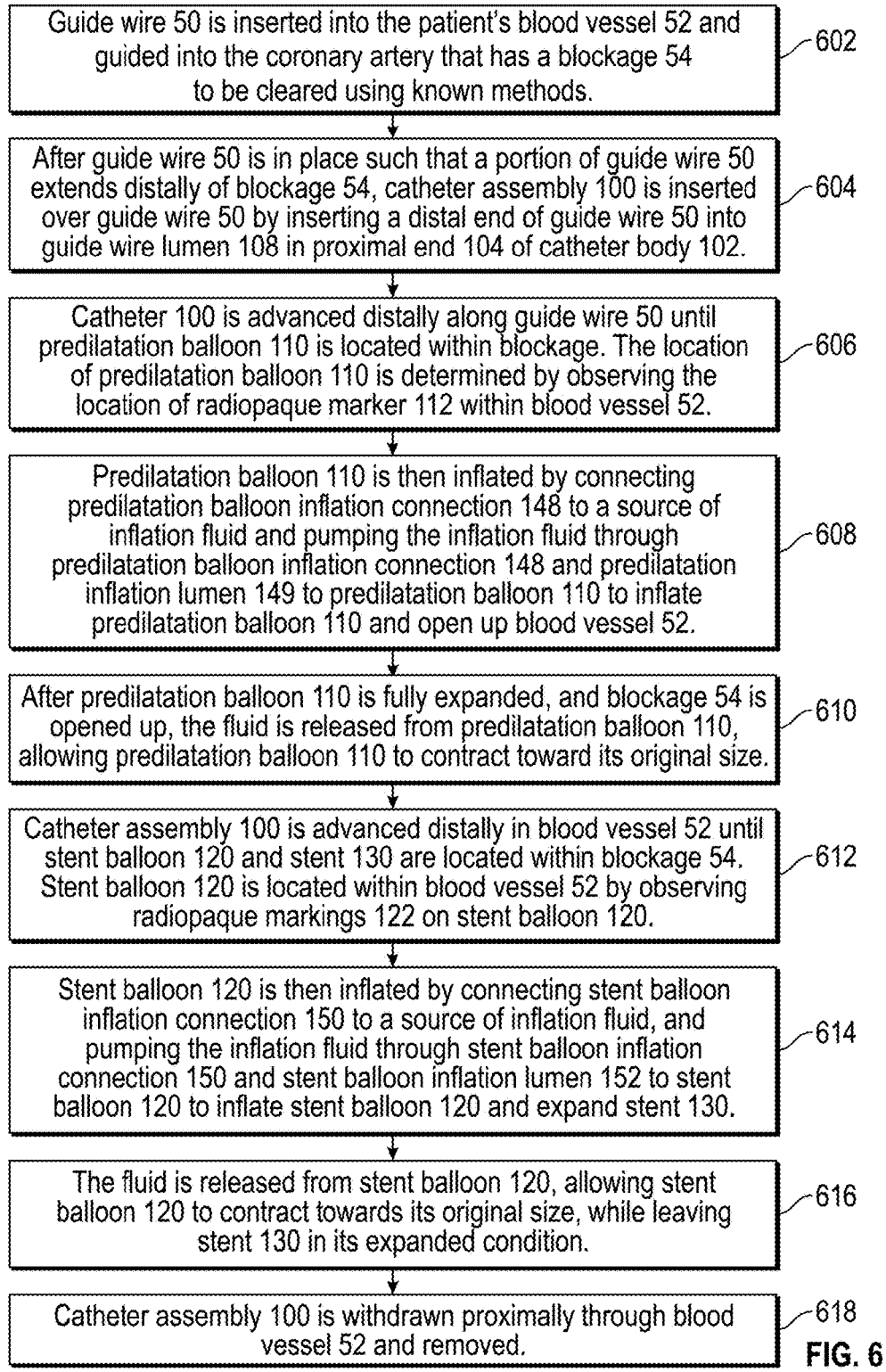
FIG. 6 is a flow chart illustration an exemplary operation of the sheathless catheter assembly of FIG. 1.
Figure 7:
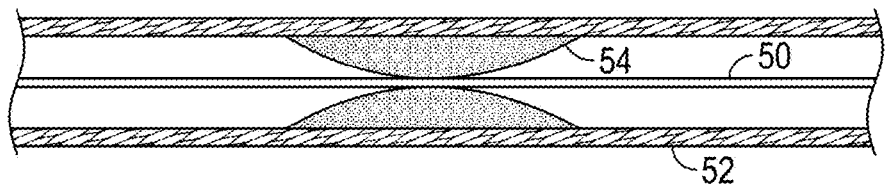
FIG. 7 is a side elevational view, in section, of a coronary artery showing a guide wire being passed through a blockage in the artery.

To use catheter assembly 100, and as explained in flowchart 600 of FIG. 6, in step 602, guide wire 50 is inserted into the patient's blood vessel 52, such as, for example, through a femoral artery, and guided into the coronary artery that has a blockage 54 to be cleared using known methods, as shown in FIG. 7. After guide wire 50 is in place such that a portion of guide wire 50 extends distally of blockage 54, in step 604, catheter assembly 100 is inserted over guide wire 50 by inserting a distal end of guide wire 50 into guide wire lumen 108 in proximal end 104 of catheter body 102.

Figure 8:
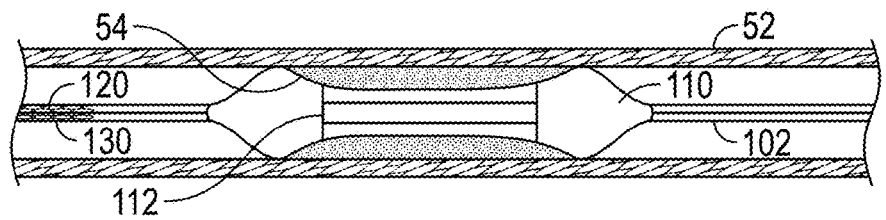
FIG. 8 is a side elevational view, in section, of the coronary artery of FIG. 8, with a predilatation balloon of the sheathless catheter assembly of FIG. 1 inflated at the site of the blockage.

In step 606, catheter 100 is advanced distally along guide wire 50 until predilatation balloon 110 is located within blockage 54, as shown in FIG. 8. The location of predilatation balloon 110 is determined by observing the location of radiopaque marker 112 within blood vessel 52 using known techniques. Predilatation balloon 110 is then inflated in step 608 by connecting predilatation balloon inflation connection 148 to a source of inflation fluid (not shown), and pumping the inflation fluid through predilatation balloon inflation connection 148 and predilatation inflation lumen 149 to predilatation balloon 110 to inflate predilatation balloon 110 and open up blood vessel 52, as shown in FIG. 8.

After predilatation balloon 110 is fully expanded, and blockage 54 is opened up, in step 610, the fluid is released from predilatation balloon 110, allowing predilatation balloon 110 to contract toward its original size. In step 612, catheter assembly 100 is advanced distally in blood vessel 52 until stent balloon 120 and stent 130 are located within blockage 54. Stent balloon 120 is located within blood vessel 52 by observing radiopaque markings 122 on stent balloon 120.

Figure 9:
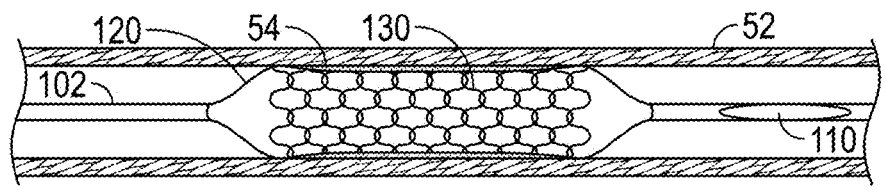
FIG. 9 is a side elevational view, in section, of the coronary artery of FIG. 8, with a stent inflation balloon of the sheathless catheter assembly of FIG. 1 inflated to expand a stent at the site of the blockage.

In step 614, stent balloon 120 is then inflated by connecting stent balloon inflation connection 150 to a source of inflation fluid (not shown), and pumping the inflation fluid through stent balloon inflation connection 150 and stent balloon inflation lumen 152 to stent balloon 120 to inflate stent balloon 120 and expand stent 130, as shown in FIG. 9. In step 616, the fluid is released from stent balloon 120, allowing stent balloon 120 to contract toward its original size, while leaving stent 130 in its expanded condition. In step 618, catheter assembly 100 is withdrawn proximally through blood vessel 52 and removed.

The inventive catheter assembly and method of the present invention obviates the need for two or more catheters, along with several catheter exchanges or manipulations to perform the method. This in turn decreases the chance of losing the position of the guide wire during the catheter balloon extraction. Further, increased pushability and turgor of the inventive assembly may improve the ease of advancing the catheter through calcific and tortuous arteries, especially when part of the inventive catheter assembly is already distally past the blockage.

Additionally, the lower cost of a single catheter, along with less time and radiation exposure required for catheter laboratory (Cath Lab) personnel may significantly decrease the cost of an angioplasty procedure. Further, patient safety and convenience may be enhanced by eliminating exchanges of catheters over the guide wire.

An alternative embodiment of a catheter assembly 200 according to the present invention is shown in FIGS. 10-16. Catheter assembly 200 is used to install a stent valve as a replacement for a damaged or calcified coronary valve. Catheter assembly 200 incorporates a valvuloplasty balloon and a self-expanding stent valve in the same assembly, eliminating the need for separate insertions of a valvuloplasty balloon and a stent valve by separate catheters or other insertion devices. Catheter assembly 200 reduces the amount of catheters required to perform a stent valve insertion procedure, reducing the risk of injury to the patient.

Catheter assembly 200 has a unitary catheter body 202 that incorporates a valvuloplasty balloon 210 at a distal end 204 of body 202 and a self-expanding stent valve 230 located proximally of valvuloplasty balloon 210. In an exemplary embodiment, valvuloplasty balloon 210 has a deflated diameter of between about 18 millimeters and about 25 millimeters and a length of about 5 centimeters. Also, valvuloplasty balloon 210 can include a radiopaque marker 212 disposed on an exterior thereof to allow for imaging and locating valvuloplasty balloon 210 within a chamber of a heart 62, such as a left ventricle, during a radiographic or fluoroscopic procedure.

In an exemplary embodiment, stent valve 230 is located a length "L" of about 5 millimeters proximally from valvuloplasty balloon 210. In an exemplary embodiment, the distance between distal end 204 and stent valve 230 is minimized because catheter assembly 200 is at least partially inserted into a patient's heart to deploy stent valve 230 across a heart valve 64, leaving little room for distal end 204 in the heart 62.

In an exemplary embodiment, catheter body 202 can be constructed from polytetrafluoroethylene, although those skilled in the art will recognize that catheter body 202 can be constructed from other material. Further, valvuloplasty balloon 210 inflates upon introduction of an inflation fluid therein, and contract toward its original size upon release or withdrawal of the inflation fluid from inside of valvuloplasty balloon 210.

Figure 11:
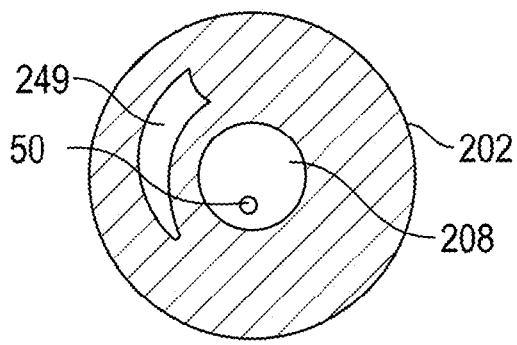
FIG. 11 is a sectional view of the valvuloplasty catheter assembly of FIG. 10, taken along lines 11-11 of FIG. 10.

Catheter assembly 200 also includes a proximal end 206. As shown in FIG. 11, catheter assembly 200 includes a guide wire lumen 208 that extends from proximal end 206, through catheter body 202, to distal end 204. Guide wire lumen 208 is sized to allow a guide wire 50 to extend fully therethrough between proximal end 202 and distal end 204.

Figure 12:
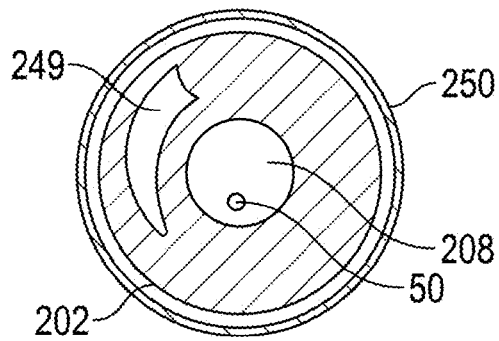
FIG. 12 is a sectional view of the valvuloplasty catheter assembly of FIG. 10, taken along lines 12-12 of FIG. 10.
Figure 13:
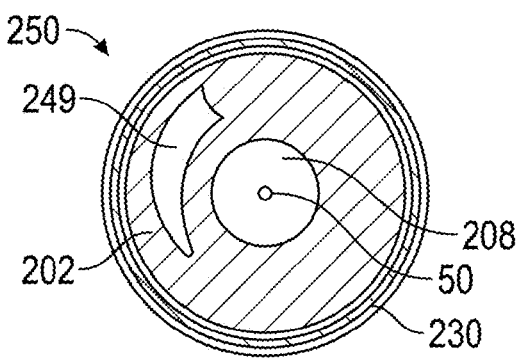
FIG. 13 is a sectional view of the valvuloplasty catheter assembly of FIG. 10, taken along lines 13-13 of FIG. 10.

A valvuloplasty balloon inflation connection 248 is located distally of proximal end 206. Valvuloplasty balloon inflation connection 248 is releasably connectable to an inflation source (not shown) that provides an inflation fluid such as, for example, saline, to inflate valvuloplasty balloon 210. As shown in FIGS. 11-13, a valvuloplasty inflation lumen 249 extends partially through catheter body 202 and provides fluid communication between valvuloplasty balloon inflation connection 248 and valvuloplasty balloon 210.

Figure 14:
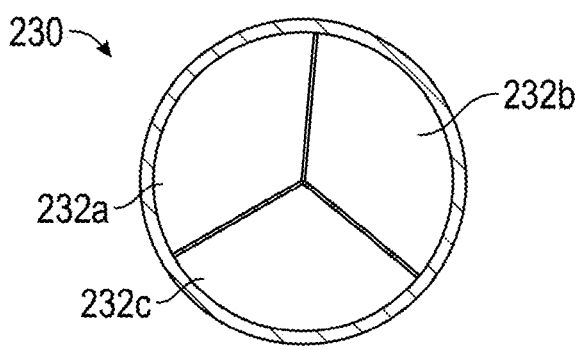
FIG. 14 is a front elevational view of a valve used with the catheter assembly of FIG. 10 after valve deployment.

In an exemplary embodiment, as shown in FIG. 14, stent valve 230 is a tricuspid one-way valve having valve flaps 232a, 232b, 232c that are operable between a closed position in which blood flow is restricted from passing through stent valve 230, and an open position in which blood flow is allowed to pass through stent valve 230.

Referring back to FIGS. 10, 12, and 13, a stent sheath 250 is disposed at least partially over catheter body 202, including over stent valve 230. Stent sheath 250 extends proximally toward predilatation balloon inflation connection 248, and can optionally include a handle 252 that allow stent sheath 250 to be slid proximally along catheter body 202 to release stent valve 230. In the event that stent valve 230 needs to be repositioned while stent valve 230 is still disposed over catheter body 202, sheath 250 can be slid distally with respect to catheter body 202 to compress stent valve 230 within sheath 250.

Figure 10:
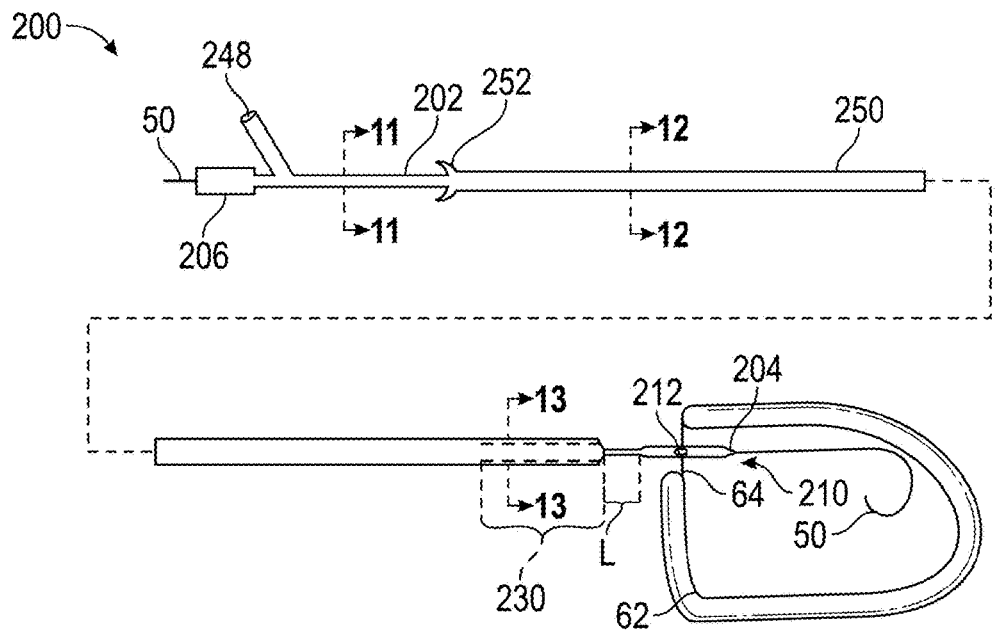
FIG. 10 is a side elevational view of a valvuloplasty catheter assembly with a self-expanding stent valve according to a second embodiment of the present invention.

To use catheter assembly 200, as shown in FIG. 10, using known methods, guide wire 50 is inserted into the patient's blood vessel, such as, for example, through a femoral artery, and guided toward heart 62 to the heart valve 64 that has a blockage to be cleared. After guide wire 50 is in place such that a portion of guide wire 50 extends distally of heart valve 64, catheter assembly 200 is inserted over guide wire 50 by inserting a distal end of guide wire 50 into guide wire lumen 208 in proximal end 204 of catheter body 202.

Figure 15:
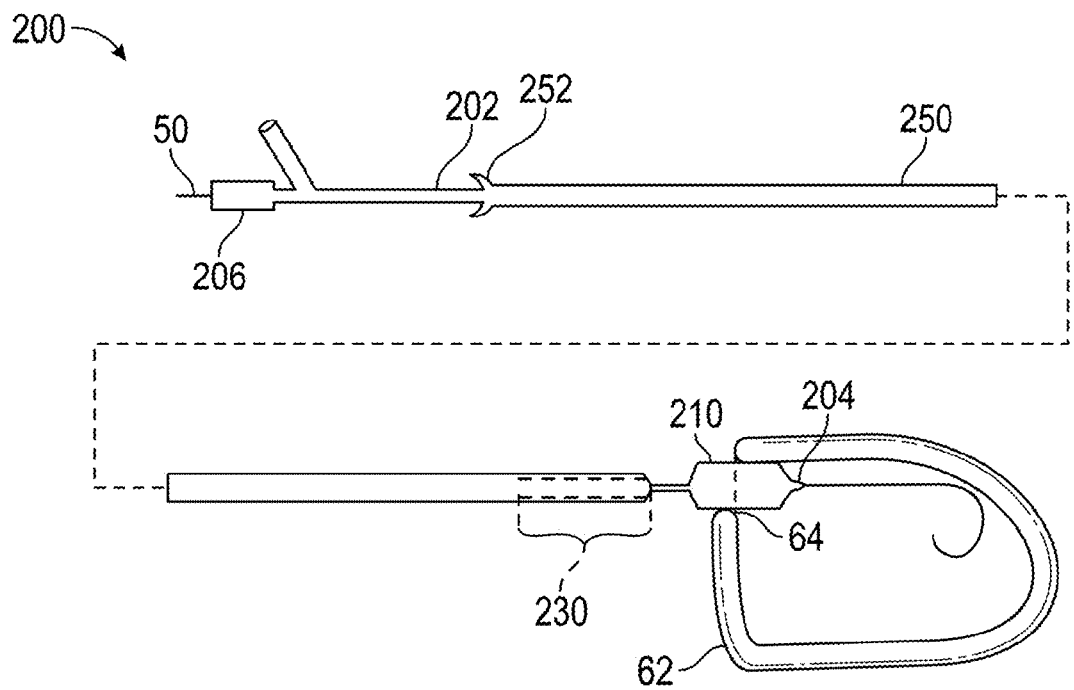
FIG. 15 is a side elevational view of the valvuloplasty catheter assembly shown in FIG. 10, with a dilatation balloon expanded across a heart valve.

Catheter assembly 200 is then advanced distally along guide wire 50 until valvuloplasty balloon 210 is located across heart valve 64, as shown in FIG. 10. The location of valvuloplasty balloon 210 is determined by observing the location of radiopaque marker 212 within heart 62 using known techniques. Valvuloplasty balloon 210 is then inflated connecting valvuloplasty balloon inflation connection 248 to a source of inflation fluid (not shown), and pumping the inflation fluid through valvuloplasty balloon inflation connection 248 and valvuloplasty inflation lumen 249 to valvuloplasty balloon 210 to inflate valvuloplasty balloon 210 and open up heart valve 64, as shown in FIG. 15.

Figure 16:
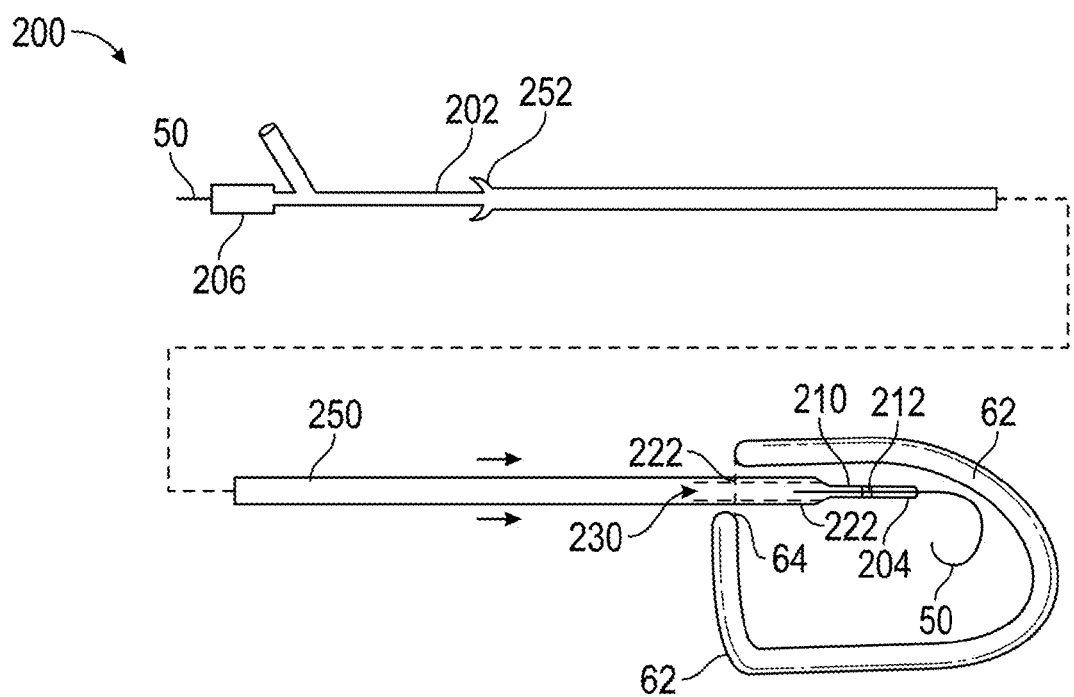
FIG. 16 is a side elevational view of the valvuloplasty catheter assembly shown in FIG. 10, with a sheathed valve located across the heart valve.

After valvuloplasty balloon 210 is fully expanded, and valve 64 is opened up, the fluid is released from valvuloplasty balloon 210, allowing valvuloplasty balloon 210 to contract toward its original size. Catheter assembly 200 is next advanced distally into heart 62 until stent valve 230 is located within across valve 64, as shown in FIG. 16. Stent valve 230 is advanced across valve 64 by radioscopically observing stent valve 230, which is radiopaque.

Figure 17:
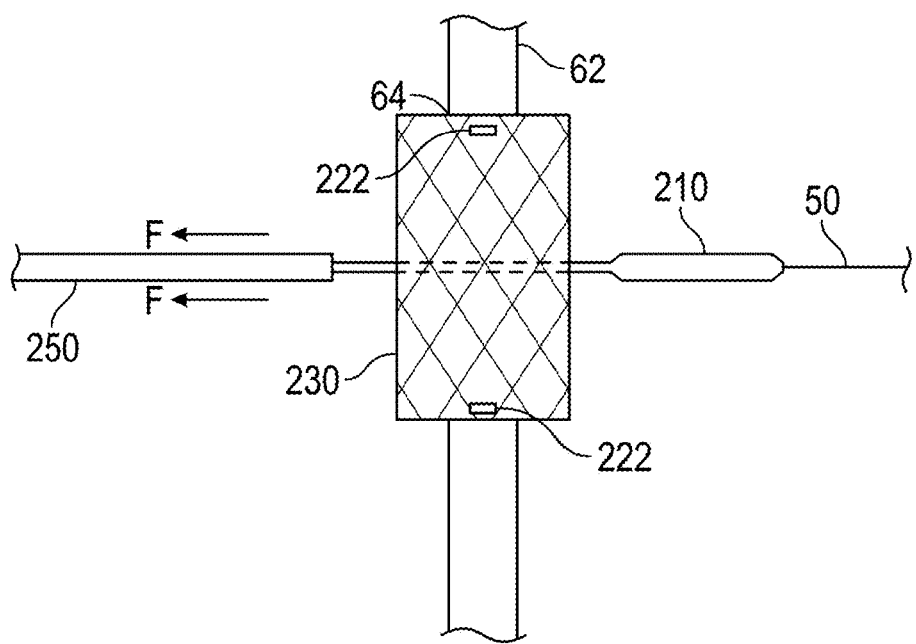
FIG. 17 is an enlarged elevational view of the valvuloplasty catheter assembly shown in FIG. 10, with the sheath retracted and the valve expanded across the heart valve.
Figure 18:
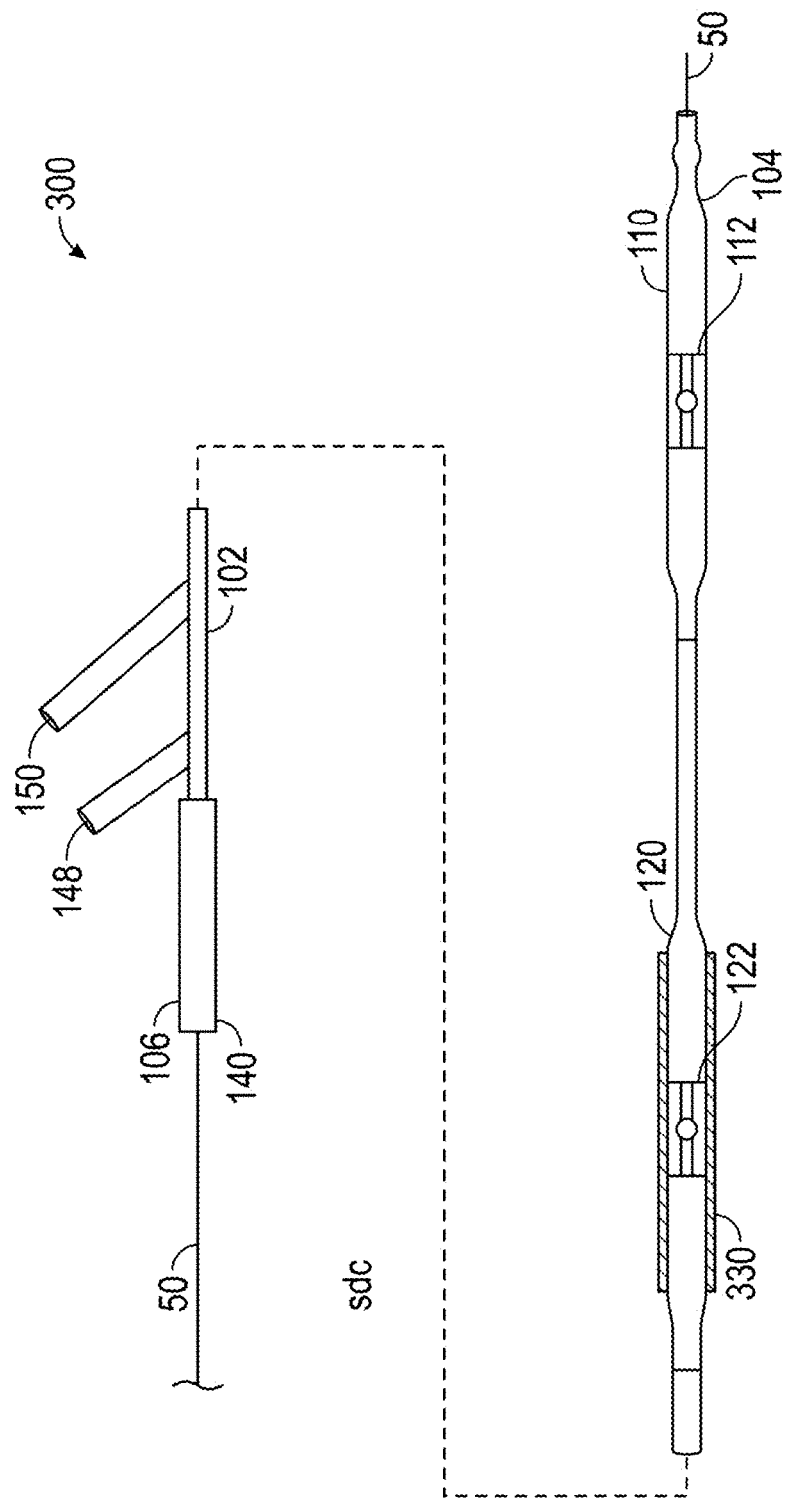
FIG. 18 is a side elevational view of a valvuloplasty catheter assembly with a balloon expandable stent valve according to a third embodiment of the present invention.

As shown in FIG. 17, valve 230 is expanded by withdrawing stent sheath 250 proximally in the direction of arrows "F", allowing stent valve 230 to self-expand across valve 64. Next, catheter assembly 200 is withdrawn proximally through the blood vessel and removed.

Alternatively, instead of a balloon expanding stent 130, a catheter assembly 300 incorporates a balloon expandable stent valve 330. In catheter assembly 300, stent valve 330 is advanced to heart valve 64 in the same manner as described with respect to stent valve 230 above. However, instead of sliding sheath 250 proximally, stent valve balloon 120 is inflated to expand stent valve 330 across heart valve 64. In this embodiment, stent valve balloon 120 is located about 5 millimeters proximal of valvuloplasty balloon 310.

An alternative embodiment of a catheter assembly 400 according to the present invention is shown in FIGS. 19-27. Catheter assembly 400 is used to open up blockages within coronary arteries and is similar to catheter assembly 100, but, instead of having a guide wire lumen 408 extending wholly through a catheter body 402 between a distal end 404 and a proximal end 406, catheter assembly 400 can be a "rapid exchange" catheter in which guide wire lumen 408 extends through catheter body 402 distally of a stent balloon inflation connection 450 and extends through catheter body 402 to distal end 404 of catheter body 402.

An advantage of catheter assembly 400 is that catheter assembly 400 is wholly self-contained, meaning that no other instruments such as sheaths or other catheters are required to be used with catheter 400. As such, catheter assembly 400 is a "standalone" device.

Similar to catheter assembly 100, catheter assembly 400 is specifically designed for use within narrow coronary arteries that have an inside diameter of typically 6 French or less. The fact that catheter assembly 400 is sheathless allows catheter assembly 400 to be inserted into such narrow arteries. Sheathed catheters are too wide in diameter to fit into these arteries, given the additional width of the sheath itself.

Catheter assembly 400 has a unitary catheter body 402 that incorporates a predilatation balloon 410 at a distal end 404 of body 402 and a combination stent balloon 420 and stent 430 are located proximally of predilatation balloon 410. In an exemplary embodiment, predilatation balloon 410 has a deflated diameter of about 2.5 millimeters and a length of about 15 millimeters. Also, stent balloon 410 can include a radiopaque marker 412 disposed on an exterior thereof to allow for imaging and locating stent balloon 410 within a blood vessel 52 (shown in FIG. 26) during an angioplasty procedure.

In an exemplary embodiment, stent balloon 420 and stent 430 are located between about 5 millimeters and about 15 millimeters proximally from predilatation balloon 410. More specifically, stent balloon 420 and stent 430 are located about 5 millimeters proximally from predilatation balloon 410. The small distance of about 5 millimeters can be important when advancing catheter assembly 400 through a blood vessel 52, particularly a small coronary vessel that may not have much distance between a blockage that is being treated and a patient's heart.

In an exemplary embodiment, catheter body 402 can be constructed from polytetrafluoroethylene, although those skilled in the art will recognize that catheter body 402 can be constructed from other material. Further, each of predilatation balloon 410 and stent balloon 420 inflate upon introduction of an inflation fluid therein, and contract toward their original size upon release or withdrawal of the inflation fluid from inside each of predilatation balloon 410 and stent balloon 420.

Catheter assembly 400 also includes a proximal end 406. A predilatation balloon inflation connection 448 is located at proximal end 406. Predilatation balloon inflation connection 448 is releasably connectable to an inflation source (not shown) that provides an inflation fluid such as, for example, saline, to inflate predilatation balloon 410. As shown in FIGS. 20-23 and 25, a predilatation inflation lumen 449 provides fluid communication between predilatation balloon inflation connection 448 and predilatation balloon 410. Predilatation inflation lumen 449 extends through stent balloon 420.

A stent balloon inflation connection 450 is located distally of predilatation balloon inflation connection 448. While stent balloon inflation connection 450 is shown as being located distally of predilatation balloon inflation connection 448, those skilled in the art will recognize that stent balloon inflation connection 450 can be located proximally of predilatation balloon inflation connection 448 without departing from the scope of the present invention.

Figure 21:
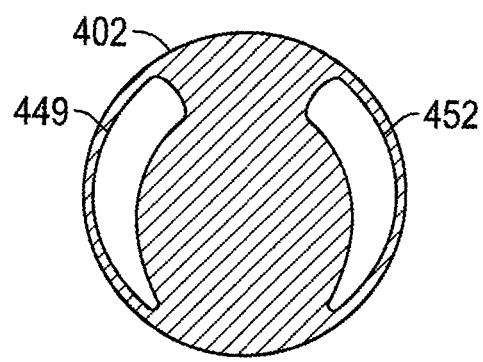
FIG. 21 is a sectional view of the sheathless catheter assembly of FIG. 19, taken along lines 21-21 of FIG. 19.
Figure 22:
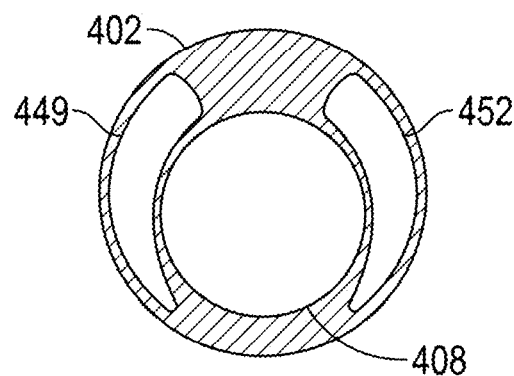
FIG. 22 is a sectional view of the sheathless catheter assembly of FIG. 19, taken along lines 22-22 of FIG. 19.
Figure 23:
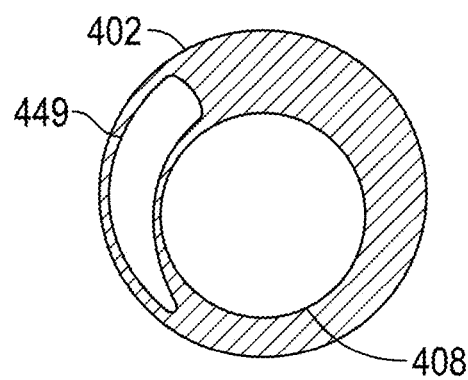
FIG. 23 is a sectional view of the sheathless catheter assembly of FIG. 19, taken along lines 23-23 of FIG. 19.
Figure 24:
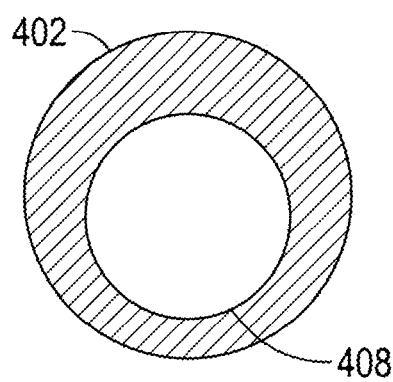
FIG. 24 is a sectional view of the sheathless catheter assembly of FIG. 19, taken along lines 24-24 of FIG. 19.
Figure 25:
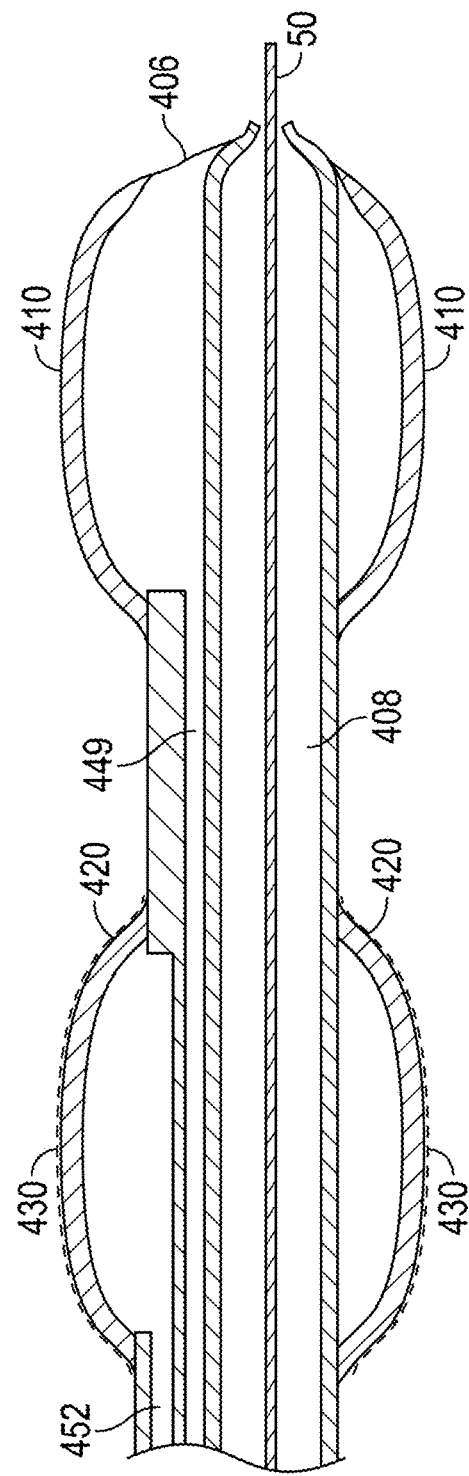
FIG. 25 is a sectional view of the sheathless catheter assembly of FIG. 19, taken along lines 25-25 of FIG. 19.
Figure 26:
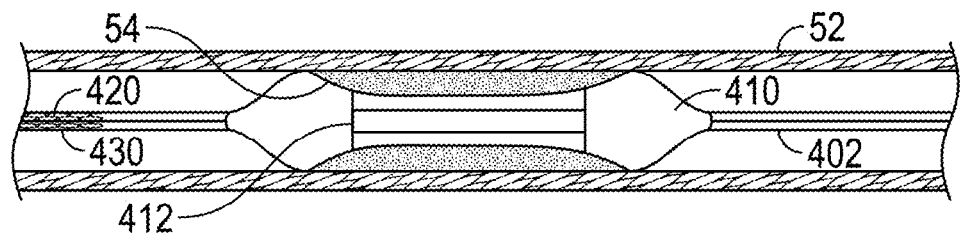
FIG. 26 is a side elevational view, in section, of the coronary artery of FIG. 7, with a predilatation balloon of the sheathless catheter assembly of FIG. 19 inflated at the site of the blockage.
Figure 27:
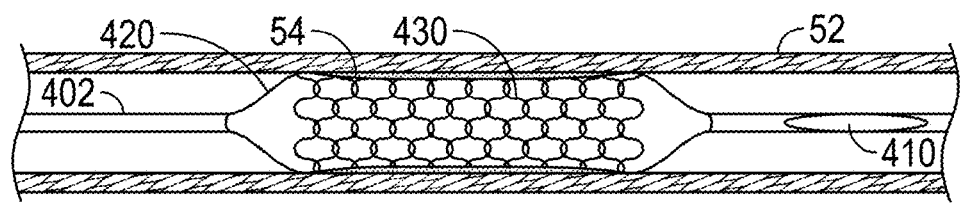
FIG. 27 is a side elevational view, in section, of the coronary artery of FIG. 7, with a stent inflation balloon of the sheathless catheter assembly of FIG. 19 inflated to expand a stent at the site of the blockage.

Stent balloon inflation connection 450 is releasably connectable to an inflation source (not shown) that provides an inflation fluid such as, for example, saline, to inflate stent balloon 420. The same fluid source that is used to inflate predilatation balloon 410 can be used to inflate stent balloon 420. As shown in FIGS. 21, 22, and 25, a stent balloon inflation lumen 452 provides fluid communication between stent balloon inflation connection 450 and stent balloon 420. Referring back to FIG. 19, stent balloon 420 includes at least one radiopaque marker 422 that allows the treating physician to locate stent balloon 420 within blood vessel 52 (shown in FIG. 27).

Stent 430 is an expandable stent as is well known in the art. Stent 430 is not self-expanding, but is expanded by the inflation of stent balloon 420. Stent 430 remains expanded after stent balloon 420 is deflated. Further, in an exemplary embodiment, stent 430 has an expanded size of customarily known, industry standard, and well-used coronary stents within typical ranges of between about 2.5 millimeters and about 4 millimeters in diameter and between about 12 millimeters and about 33 millimeters in length. Additionally, in an exemplary embodiment, stent 430 does not include a graft, although those skilled in the art will recognize that a graft may be utilized with stent 430.

As shown in FIGS. 22-25, catheter assembly 400 includes a guide wire lumen 408 that extends through body 402 from an opening 409 distal of stent balloon inflation connection 450 and extending through the body to distal end 404 of body 402. In an exemplary embodiment, opening 409 is about 24.5 cm from distal end 404 of catheter body 402.

Guide wire lumen 408 is sized to allow a guide wire 50 to extend partially through body 402, between opening 409 and distal end 404. The location of opening 409 distally of stent balloon inflation connection 450 allows for the rapid exchange of catheter 400 over guide wire 50. A benefit of the rapid exchange of catheter 400 is that such exchange can be performed faster, and importantly, safer, since a significant portion of catheter assembly 400 can be pulled back by merely holding the guide wire in place. Once the catheter shaft is reached, the exchange is performed under fluoroscopy in a known way (pushing guide wire 50 and pulling catheter assembly 400) until distal tip 406 of catheter assembly 400 is removed from blood vessel 52.

Figure 19:
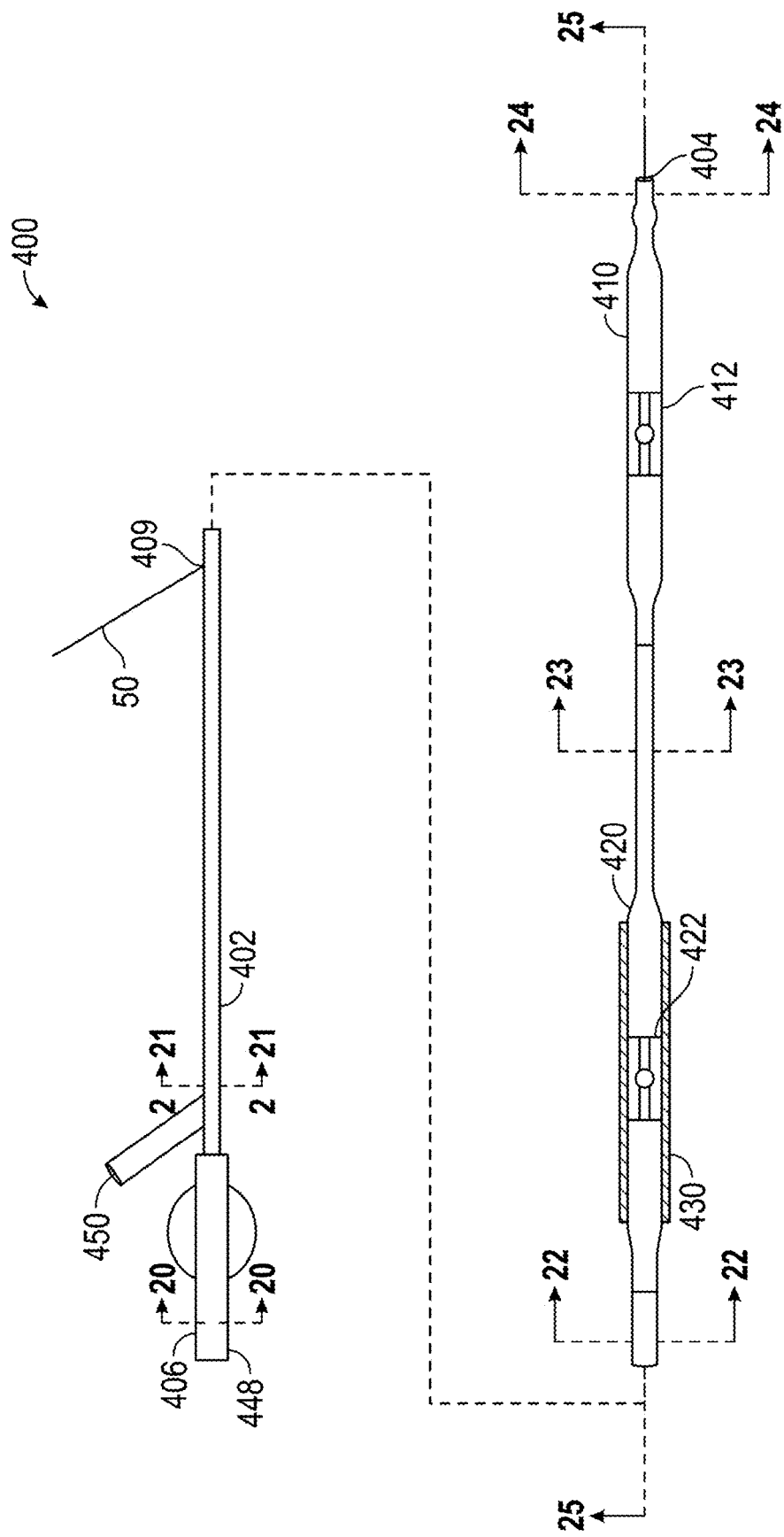
FIG. 19 is a side elevational view of a sheathless catheter assembly according to a third embodiment of the present invention.
Figure 20:
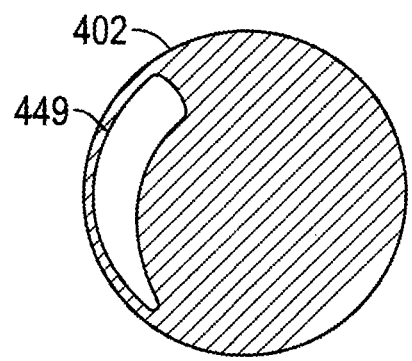
FIG. 20 is a sectional view of the sheathless catheter assembly of FIG. 19, taken along lines 20-20 of FIG. 19.

Guide wire 50 is inserted into blood vessel 52 in a known manner such that guide wire extends on either side of a blockage 54, as shown in FIG. 7. The insertion and operation of catheter assembly 400 is the same as the insertion and operation of catheter assembly 100 as described above, as well as in FIG. 6, substituting element numbers beginning with "1" with element numbers beginning with "4". However, instead of guide wire 50 exiting catheter body 402 at proximal end 406, guide wire 50 exits body 402 through opening 409 distal of stent balloon inflation connection 450, as is shown in FIG. 19.

Figure 28:
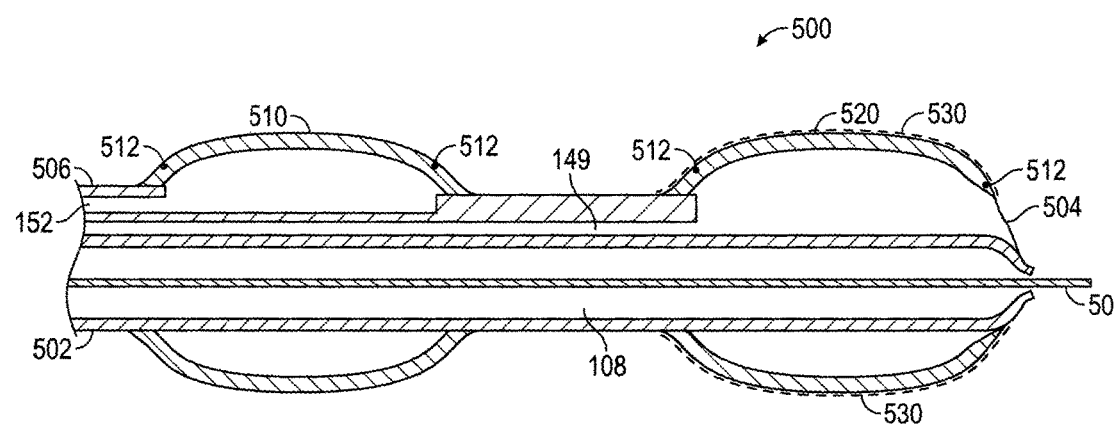
FIG. 28 is a side elevational view, in section, of a sheathless catheter assembly according to a fourth embodiment of the present invention.
Figure 29:
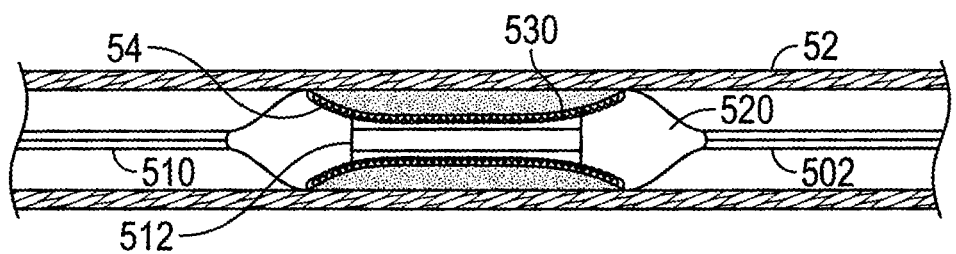
FIG. 29 is a side elevational view of the coronary artery of FIG. 7, with a stent balloon of the sheathless catheter assembly of FIG. 20 inflated at the site of the blockage.
Figure 30:
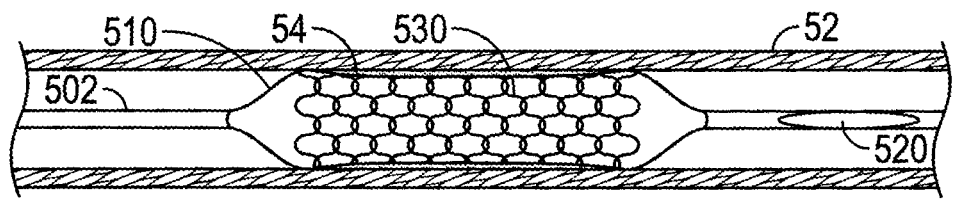
FIG. 30 is a side elevational view of the coronary artery of FIG. 7, with a post-dilatation balloon of the sheathless catheter assembly of FIG. 28 inflated to expand the stent of FIG. 29 at the site of the blockage.

Referring to FIGS. 28-30, another exemplary embodiment of a catheter assembly 500 according to the present invention is shown. Catheter assembly 500 is used to open up blockages within coronary arteries.

Catheter assembly 500 is specifically designed for use within narrow coronary arteries that have an inside diameter of typically 6 French or less. The fact that catheter assembly 500 is sheathless allows catheter assembly 100 to be inserted into such narrow arteries. Sheathed catheters are too wide in diameter to fit into these arteries, given the additional width of the sheath itself.

Catheter assembly 500 has a unitary, monolithic, catheter body 502 that incorporates a combination stent balloon 520 and stent 530 at a distal end 504 of body 502 and a post-dilatation balloon 510 located proximally of combination stent balloon 520 and stent 530.

In an exemplary embodiment, post-dilatation balloon 510 has a deflated diameter of about 2.5 millimeters and a length of about 15 millimeters. Post-dilatation balloon 510 can be constructed from a non-compliant material, such as, for example, a nylon non-compliant balloon material.

Also, each of post-dilatation balloon 510 and stent balloon 520 can include radiopaque markers 512 disposed on an exterior thereof to allow for imaging and locating post-dilatation balloon 510 and stent balloon 520 within a blood vessel 52 (shown in FIGS. 29 and 30) during an angioplasty procedure.

In an exemplary embodiment, stent balloon 520 and stent 530 are located between about 10 millimeters and about 15 millimeters distally from post-dilatation balloon 510. In an exemplary embodiment, catheter body 502 can be constructed from polytetrafluoroethylene, although those skilled in the art will recognize that catheter body 502 can be constructed from other material. Further, each of post-dilatation balloon 510 and stent balloon 520 inflate upon introduction of an inflation fluid therein, and contract toward their original size upon release or withdrawal of the inflation fluid from inside each of post-dilatation balloon 510 and stent balloon 520.

Catheter assembly 500 also includes a proximal end 506 similar to proximal end 106 of catheter assembly 100 as described above. Catheter 500 also includes guide wire lumen 108, a post-dilatation balloon inflation lumen 152 that provides inflation fluid to post-dilatation balloon 510, and a stent balloon inflation lumen 149 that provides inflation fluid to stent balloon 120.

Stent 530 is an expandable, bioabsorbable stent as is well known in the art. Stent 530 is not self-expanding, but is expanded by the inflation of stent balloon 520. Stent 530 remains expanded after stent balloon 520 is deflated. Further, in an exemplary embodiment, stent 530 has an expanded size of customarily known, industry standard, and well-used coronary stents within typical ranges of between about 2.5 millimeters and about 4 millimeters in diameter and between about 12 millimeters and about 33 millimeters in length. Additionally, in an exemplary embodiment, stent 530 does not include a graft, although those skilled in the art will recognize that a graft may be utilized with stent 530.

Figure 31:
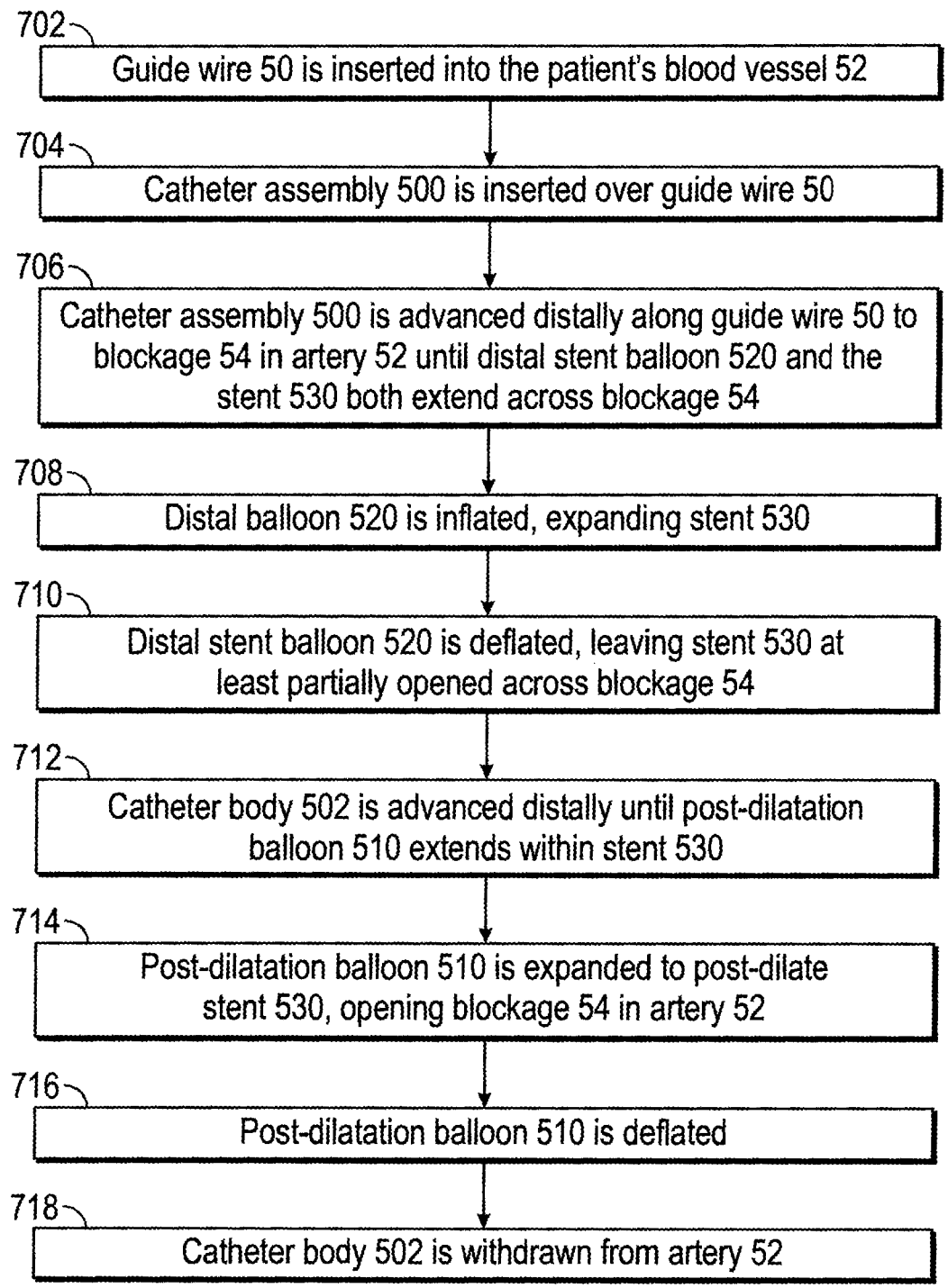
FIG. 31 is a flowchart illustrating an exemplary operation of the catheter assembly of FIG. 28.

To use catheter assembly 500, and as explained in flowchart 700 of FIG. 31, in step 702, guide wire 50 is inserted into the patient's blood vessel 52, such as, for example, through a femoral artery, and guided into the coronary artery that has a blockage 54 to be cleared, as shown in FIGS. 29 and 30. After guide wire 50 is in place such that a portion of guide wire 50 extends distally of blockage 54, in step 704, catheter assembly 500 is inserted over guide wire 50.

In step 706, catheter assembly 500 is advanced distally along guide wire 50 to blockage 54 in artery 52 until distal stent balloon 520 and the stent 530 both extend across blockage 54. In step 708, as shown in FIG. 29, distal balloon 520 is inflated, expanding stent 530. In step 710, distal stent balloon 520 is deflated, leaving stent 530 at least partially opened across blockage 54.

In step 712, catheter body 502 is advanced distally until post-dilatation balloon 510 extends within stent 530. In step 714, as shown in FIG. 30, post-dilatation balloon 510 is expanded to post-dilate stent 530, opening blockage 54 in artery 52. In step 716, post-dilatation balloon 510 is deflated. In step 718, catheter body 502 is withdrawn from artery 52.

The inventive catheter assembly and method of the present invention obviates the need for two or more catheters, along with several catheter exchanges or manipulations to perform the method. This in turn decreases the chance of losing the position of the guide wire during the catheter balloon extraction. Further, increased pushability and turgor of the inventive assembly may improve the ease of advancing the catheter through calcific and tortuous arteries, especially when part of the inventive catheter assembly is already distally past the blockage.

Additionally, the lower cost of a single catheter, along with less time and radiation exposure required for catheter laboratory (Cath Lab) personnel may significantly decrease the cost of an angioplasty procedure. Further, patient safety and convenience may be enhanced by eliminating exchanges of catheters over the guide wire.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method of inserting a stent comprising the steps of, in order:
   (a) inserting no more than a single, monolithic catheter over a single guide wire into a cardiac artery, the catheter comprising:
      (i) a unitary catheter body having a proximal end and a distal end, and a first lumen, a second lumen, and a third lumen formed in the body;
      (ii) a distal balloon directly attached to the distal end of the catheter body, the distal balloon being in fluid communication with the first lumen;
      (iii) a proximal balloon directly attached to the catheter body, proximally of the distal balloon, the proximal balloon being in fluid communication with the second lumen; and
      (iv) a balloon expandable stent having a proximal end, the stent being mounted on the distal balloon such that the proximal end of the stent is located distal of the proximal balloon;
   (b) advancing the catheter over the single guide wire to a blockage in the artery until the distal balloon and the stent both extend across the blockage;
   (c) inflating the distal balloon and expanding the stent;
   (d) deflating the distal balloon and disengaging the distal balloon from the stent;
   (e) further advancing the catheter body distally until the proximal balloon extends within the stent;
   (f) expanding the proximal balloon to post-dilate the stent;
   (g) deflating the proximal balloon; and
   (h) withdrawing the catheter body from the artery.

2. The method according to claim 1, wherein step (a) comprises the stent being a bio-absorbable stent.

3. The method according to claim 1, wherein step (a) comprises the proximal balloon being constructed from a non-compliant material.

4. The method according to claim 3, wherein step (a) comprises the proximal balloon being constructed from polytetrafluoroethylene nylon material.

5. The method according to claim 1, wherein step (h) further comprises withdrawing the catheter over the single guide wire.

6. A method of inserting a catheter into a single blood vessel, the method comprising the steps of:
   (a) providing a catheter having:
      (i) a unitary catheter body having a proximal end and a distal end;
      (ii) a distal balloon directly attached to the distal end of the catheter body;
      (iii) a proximal balloon directly attached to the catheter body, proximally of the distal balloon;
      (iv) a first lumen extending only partially through the body and in fluid communication with the distal balloon;
      (v) a second lumen extending only partially through the body and in fluid communication with the proximal balloon;
      (vi) a third lumen extending to the distal end of the body; and
      (vii) a balloon expandable stent having a proximal end, the stent being mounted on the distal balloon such that the proximal end of the stent is located distally of the proximal balloon;
   (b) inserting the guide wire into the third lumen and advancing the catheter assembly over the single guide wire to a blockage in the single blood vessel until the distal balloon and the stent both extend across the blockage;
   (c) inflating the distal balloon and expanding the stent;
   (d) deflating the distal balloon and disengaging the distal balloon from the stent;
   (e) further advancing the catheter body distally until the proximal balloon extends within the stent;
   (f) expanding the proximal balloon to post-dilate the stent;
   (g) deflating the proximal balloon; and
   (h) withdrawing the catheter body from the artery.

7. A method of inserting a catheter into a single blood vessel, the method comprising the steps of:
   (a) providing a catheter having:
      (i) a unitary catheter body having a proximal end and a distal end;
      (ii) a distal balloon directly attached to the distal end of the catheter body, the distal balloon having a distal balloon length;
      (iii) a proximal balloon directly attached to the catheter body, proximally of the distal balloon;
      (iv) a first lumen extending only partially through the body and in fluid communication with the distal balloon;
      (v) a second lumen extending only partially through the body and in fluid communication with the proximal balloon;

(vi) a third lumen extending to the distal end of the body; and
(vii) a balloon expandable stent disposed on the distal balloon, a proximal end of the stent at a proximal end of the distal balloon;
(b) inserting the guide wire into the third lumen and advancing the catheter assembly over the single guide wire to a blockage in the single blood vessel until the distal balloon and the stent both extend across the blockage;
(c) inflating the distal balloon and expanding the stent;
(d) deflating the distal balloon and disengaging the distal balloon from the stent;
(e) further advancing the catheter body distally until the proximal balloon extends within the stent;
(f) expanding the proximal balloon to post-dilate the stent;
(g) deflating the proximal balloon; and
(h) withdrawing the catheter body from the artery.

* * * * *